(12) United States Patent
Kamimoto

(10) Patent No.: US 6,833,128 B2
(45) Date of Patent: Dec. 21, 2004

(54) METHOD FOR MONITORING LOCAL REACTION ASSOCIATED WITH INJECTIONS

(75) Inventor: Laurie Kamimoto, Atlanta, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 226 days.

(21) Appl. No.: 09/972,689

(22) Filed: Oct. 5, 2001

(65) Prior Publication Data

US 2002/0041851 A1 Apr. 11, 2002

Related U.S. Application Data

(60) Provisional application No. 60/238,691, filed on Oct. 6, 2000.

(51) Int. Cl.[7] .................................................. A61B 5/00
(52) U.S. Cl. ........................ 424/9.81; 424/9.8; 427/2.12
(58) Field of Search ................................ 424/9.8, 9.81; 427/2.12

(56) References Cited

U.S. PATENT DOCUMENTS

| 3,894,531 A | 7/1975 | Saunders, Jr. ................... 128/2 |
| 5,099,857 A | 3/1992 | Baldo et al. ................. 128/743 |
| 5,179,959 A | 1/1993 | Fishman et al. ............. 128/743 |
| 5,369,527 A | 11/1994 | McCracken ................. 359/805 |
| 5,817,385 A | 10/1998 | Stanislav .................... 428/40.2 |
| 5,928,797 A | 7/1999 | Vineberg ..................... 428/500 |
| 5,958,560 A | 9/1999 | Ewan ......................... 428/201 |
| 6,042,881 A | 3/2000 | Ewan ......................... 427/152 |
| 6,074,721 A | 6/2000 | Moore et al. .............. 428/42.1 |
| 6,106,852 A | 8/2000 | Vineberg .................... 424/402 |

OTHER PUBLICATIONS

McArthur, et al., "Safety of preoperation endoscopic tattoo with India ink for identification of colonic lesions," Surg. Endosc., vol. 4, Apr. 13, 1999, pp. 397–400 (abstract only).
Haselow & Krause, "Problems with India ink skin markings," Radiology, vol. 2, Feb. 1980, pp. 542–543 (abstract only).

*Primary Examiner*—David Saunders
(74) *Attorney, Agent, or Firm*—Klarquist Sparkman, LLP

(57) ABSTRACT

A method is disclosed for monitoring local reactions, such as inflammatory responses, associated with injection sites. The method is performed using a temporary tattoo, which is transferred from a substrate to the skin of a subject, to measure the local reaction to an injection. A kit is also disclosed that can be used to perform the disclosed method. One example of the method includes transferring from the substrate to the subject's skin a temporary tattoo having a plurality of concentric rings and using the rings to measure the local reaction. For example, if the local reaction exceeds the boundary of the largest ring, the local reaction is considered clinically significant and additional medical interventions may be sought.

13 Claims, 2 Drawing Sheets

METHOD FOR MONITORING LOCAL REACTION ASSOCIATED WITH INJECTIONS

This application claims benefit of provisional application 60/238,691, filed Oct. 6, 2000.

FIELD

A method for monitoring local reactions associated with injection sites and kit for performance of the method are disclosed. More specifically, a simple visual method for monitoring local reactions associated with injection sites, which can be utilized even in non-medical environments, and a kit for use in performing the method are disclosed. The disclosed method and kit can be used, for example, to monitor local reactions associated with a subject's vaccine injection site, and help determine whether the local reaction observed is within normal ranges. Use of the method can reduce unnecessary return medical visits due to overreaction to normal local reactions at vaccine injection sites, as well as provide assurance that a subject's local reaction is within the normal range. In cases where the local reaction exceeds the normal range, the method can provide guidance on seeking additional medical advice and/or attention.

BACKGROUND

In the United States, approximately 74 million vaccine or immunization shots are expected to be administered in 2000 as protection against various diseases. Due largely to the trend in combination immunizations, the number of immunization shots is expected to decrease to about 66 million in 2004. Many of these vaccinations will be directed at young children, especially infants. In many cases, such immunizations cause local reactions such as, for example, redness, swelling, erythema, and the like. Although such local reactions are common and generally are not medically significant (e.g., are not predictive of serious problems), many parents, especially first-time parents, become concerned when they observe such redness or swelling. Moreover, such parents often have difficulty determining whether a child's reaction to the shot is within normal limits or parameters and, thus, become needlessly concerned. Such concern, in addition to being worrisome, can also result in unnecessary clinical attention (such as doctor visits) and medical expenses.

It would be desirable, therefore, to provide a simple method to monitor local reactions due to an injection, in order to determine whether the local reaction is within normal parameters.

SUMMARY

A method is disclosed for monitoring local reactions associated with injection sites. The method provides a simple visual method for monitoring local reactions associated with injection sites, which can even be utilized by laypersons (such as parents or guardians) in non-medical environments. A kit is also provided for performing the method. The method can be used with human subjects, but could also be used with animal subjects such as horses or dogs. The disclosed method can be used, for example, by a parent to monitor local reactions associated with a child's vaccine injection site, and help determine whether a local reaction is within normal ranges. Use of the method can reduce unnecessary medical visits due to overreaction to normal local reactions at injection sites, as well as provide assurance that a local reaction is within the normal range. In cases where the local reaction exceeds the normal range, the method can provide guidance on seeking additional medical advice and/or attention.

DETAILED DESCRIPTION

Figure 1:
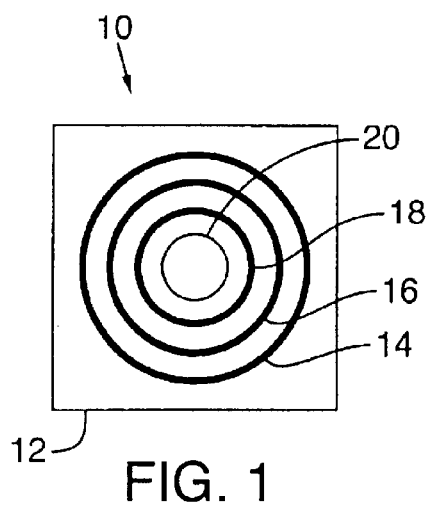
FIG. 1 illustrates a top view of one embodiment of a temporary tattoo patch.

A method is disclosed for monitoring local reactions, such as inflammatory responses, associated with injection sites. More specifically, a simple visual method is provided for monitoring local reactions associated with injection sites, which can even be utilized by laypersons (such as parents or guardians) in non-medical environments. A kit for performing the method is also provided. The disclosed method can be used, for example, to monitor local reactions associated with a child's vaccine injection site, and help determine whether a local reaction is within normal ranges. Use of the method can reduce unnecessary medical visits due to over-reaction to normal local reaction at vaccine injection sites, as well as provide assurance that a child's local reaction is within the normal range. In cases where the local reaction exceeds the normal range, the method can provide guidance on seeking additional medical advice and/or attention.

One example of the method for monitoring a local reaction due to an injection at an injection site on a subject's body is performed by first pressing a temporary tattoo transfer substrate, carrying a temporary tattoo, against a subject's skin adjacent to the injection site so that the temporary tattoo is transferred to the subject's skin. The temporary tattoo has at least one indicium for gauging the local reaction. The tattoo is applied such that the indicium is spaced from, and centered on, the injection site. Then the local reaction associated with the injection that may occur is observed. The indicium represents the extent of a normal local reaction to the injection and, if the local reaction remains within the normal reaction indicium, the local reaction is considered within normal parameters. However, if the local reaction extends beyond the normal reaction indicium, the local reaction is considered outside of normal parameters.

Another example of the method for monitoring a local reaction due to an injection at an injection site on a subject's body is performed by pressing a temporary tattoo transfer substrate against a subject's skin adjacent to the injection site so that the temporary tattoo is transferred to the subject's skin. The temporary tattoo has a plurality of indicia for gauging the local reaction. The tattoo is applied such that the indicia are spaced from, and centered on, the injection site. Then the local reaction associated with the injection that may occur is observed. At least one of the plurality of indicia represents the extent of a normal local reaction to the injection. If the local reaction remains within the normal reaction indicium the local reaction is considered within normal parameters. However, if the local reaction extends beyond the normal reaction indicium, the local reaction is considered outside of normal parameters.

The indicia used in the method may be any variety of shapes or lines, and may, but need not, form uninterrupted shapes surrounding the injection site. An indicium may, for example, form a ring surrounding the injection site. Another indicium might, for example, be a line segment some distance from the injection site. Still another indicium may, for example, be made up of a multiplicity of line segments spaced generally equidistantly from the injection site.

In the exemplary embodiments described herein, at least one indicium would mark a local reaction of clinical significance. For example, an indicium can be used to mark a statistically normal reaction to the injection. An indicium could also be placed such that the relationship between the indicium and the injection site can be used to assess a reaction to the injection such as a statistically normal reaction. An indicium might also be used, for example, to mark an abnormal reaction that elicits medical attention. Any number of additional indicia may be added, either inside or outside of the clinically significant indicium, depending on the level of sensitivity of reporting desired. For example, one embodiment contains three concentric indicia with an inner indicium representing the typical or normal reaction, a middle indicium as a caution, indicating a need to watch carefully, and an outermost indicium as the threshold limit, where, if the local reaction extends beyond the indicium, medical advice and/or attention is advised.

The method described can be used to monitor local reactions associated with a wide variety of injections, including, for example, vaccinations, immunizations, booster shots, allergy skin tests, skin tests for tuberculosis or other conditions/diseases, insect bites and stings, and the like. The method is adapted to work well for monitoring local reactions due to immunizations or vaccine shots normally given to infants and small children. Using the method, even a layperson (such as a parent or guardian) can easily determine whether the particular local reaction falls within normal parameters. If the local reaction exceeds normal parameters, and especially if it significantly exceeds normal parameters, a follow-up call or visit to a physician may be warranted. Indeed, a health care provider may schedule or arrange such a follow-up visit at the time of the initial injection, contingent upon the extent of local reaction, to help alleviate a parent's or guardian's concern with regard to local reaction. This easy method for monitoring local reactions due to vaccinations may increase parents' and guardians' confidence in immunization programs and, thus, may increase compliance rates with such immunization programs.

Figure 2:
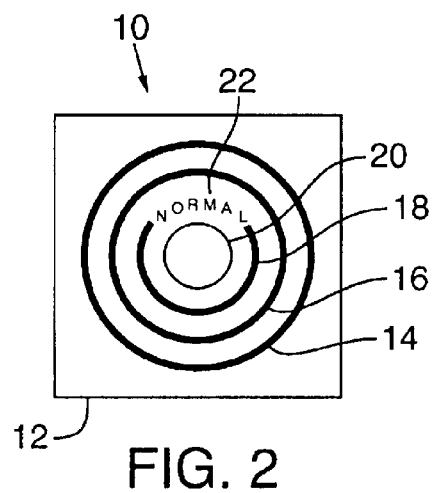
FIG. 2 is a view similar to the view in FIG. 1, but shows another embodiment of the temporary tattoo patch.

FIGS. 1 and 2 illustrate specific examples of embodiments of temporary tattoos useful in performing the method. In FIGS. 1 and 2, a temporary tattoo 10 is carried on a temporary tattoo transfer substrate 12, also known as a patch, which carries concentric circular indicia 14, 16, and 18, which are designed to surround the injection site. Indicia 18, 16, and 14 are the inner, middle, and outermost indicia, respectively. In the embodiments shown in FIGS. 1 and 2, the patch 12 has an opening 20 in the center, which is dimensioned approximately to the size of a band-aid, which will be used to cover the injection site (see band-aid 30 in FIG. 3). Opening 20 allows the temporary tattoo 10 to be easily centered on the injection site. The patch 12 may be optically clear; in that case, opening 20 would not be necessary to easily center the temporary tattoo 10 on the injection site, however, in such an embodiment it would be advantageous for the surface which is placed against the subject's skin to be sterile.

In FIGS. 1 and 2 the diameters of indicia 14, 16, and 18 are determined to mimic the size or extent of a local reaction typically expected for a specific type of vaccination or other injection. The diameters of indicia 14, 16, and 18, however, may vary depending on the specific type of vaccination or other injection given. As shown in FIG. 2, inner indicium 18 is intended to indicate the extent of a normal or typical local reaction due to the specific vaccination; of course, one of the other indicia could be used to indicate the normal or typical reaction. The "normal" indicium should be dimensioned to indicate a normal or typical local reaction. Middle and outermost indicia 16 and 14, although not specifically labeled, could be used to indicate that the injection site should be watched carefully (indicium 16) and that medical advice and/or attention is advised (outermost indicium 14). Instructions regarding the indicia could be placed directly on the tattoo or patch, or included separately in the instructions provided by a health care provider. Although the dimensions of the individual indicia can be varied as needed, typical dimensions include circles with diameters of 3, 4, and 5 centimeters.

Indicia 14, 16, and 18 in FIGS. 1 and 2 are generally circular. However, other shapes and/or designs can be used as desired, and in particular examples they are generally symmetrical with respect to the injection site and allow appropriate monitoring of the possible local reaction with respect to the injection site. As noted below, indicia 14, 16, and 18 can be colored coded using one or multiple colors. The indicia could come in a variety of shapes, designs, and/or colors so that a subject may choose his or her own tattoo. Any suitable designs could be used. Such designs might include, but are not limited to, circles or ovals formed from small star shapes, small animal shapes, individual letters spelling out names or phrases, and the like. The tattoo selection process may help relieve some of the stress or concern normally associated with "getting a shot."

Figure 4:
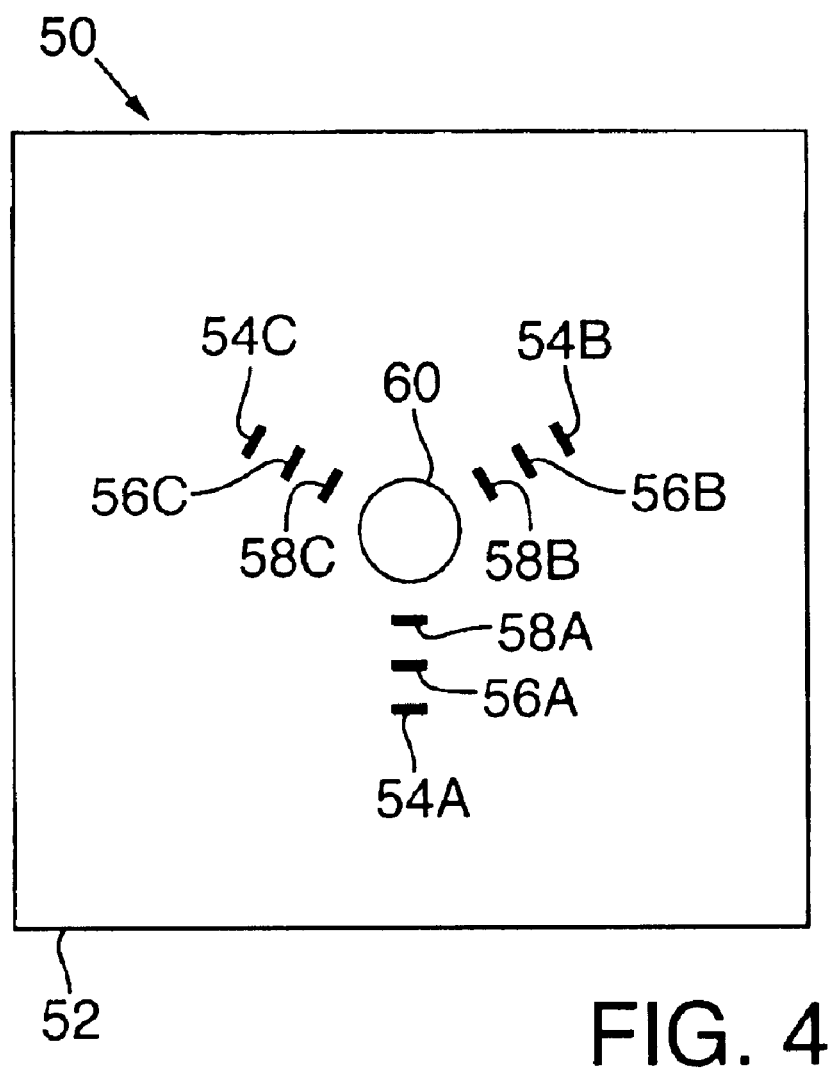
FIG. 4 illustrates a top view of another embodiment of the temporary tattoo patch.

In FIG. 4, a temporary tattoo 50 is carried on a temporary tattoo transfer substrate 52, also known as a patch, which carries indicia made up of line segments 54A, 54B, 54C, 56A, 56B, 56C, 58A, 58B, and 58C. Line segments 58A–C, 56A–C, and 54A–C make up the inner, middle, and outermost indicia respectively. The patch 52 has an opening 60 allowing the temporary tattoo to be easily centered on the injection site. In FIG. 4, line segments 54A–C, 56A–C, and 58A–C are line segments tangent to respective concentric circles. Hence, line segments 54A–C are substantially equidistant from the injection site, as are line segments 56A–C and 58A–C. The respective concentric circles to which the line segments are tangent circumscribe an expected size or extent of a local inflammatory reaction typical for a specific type of vaccination or other injection. The diameters of those concentric circles may vary depending on the specific type of vaccination or other injection given. The inner indicium, made up of line segments 58A–C, is intended to indicate the extent of a normal or typical reaction due to the specific vaccination; however, another indicium could be used to indicate the normal or typical reaction. The normal indicium could also be labeled with the word "normal" as in FIG. 2, where the word is printed on an arcuate path that replaces part of the circle. The normal indicium is ideally dimensioned to indicate a normal or typical local reaction. The middle and outermost indicia, made up of line segments 56A–C and 54A–C, respectively, could be used to indicate that the injection site should be watched carefully (indicium made up of line segments 56A–C) and that medical advice and/or attention is advised (outermost indicium made up of line segments 54A–C). Instructions regarding the indicia could be placed directly on the tattoo, the patch, or included in instructions provided by a health care provider. Although the dimensions of the concentric circles to which the line segments are tangent can be varied as needed, typical dimensions include circles with diameters of 3, 4, and 5 centimeters.

Line segments 54A–C, 56A–C, and 58A–C that make up the indicia described above are line segments tangent to respective concentric circles. However, other shapes, line or arc segments, and/or designs that generally lie along respective generally circular or elliptical paths can be used. In particular examples, the other shapes, line or arc segments, and/or designs are positioned generally symmetrically with respect to the injection site.

As noted above, the indicia can be labeled (as in FIG. 2) or unlabeled (as in FIG. 1). In either case, instructions and/or literature can be given to a monitor at the time of the injection that provide more details regarding the vaccination or other injection, the likelihood and significance of local reactions expected, and the like. Such instructions, for example could explain the significance of each of the indicia (e.g., mild, typical, significant) and desired follow-up, if any, for each type of local reaction. The instructions may also include related information regarding, for example, the need for booster shots, medical contact information in the case of greater than normal local reaction, symptoms other than local reaction that may indicate an adverse reaction, and the like. The inner indicium 18 of FIG. 2 is marked "NORMAL" to indicate a normal or typical local reaction. Other labels (such as "TYPICAL," "OK," specific colors, and the like) could be used if desired, and codes or meanings of such labels could be provided in the instructions and/or literature provided by a health care provider at the time of the injection. The indicia can be color coded using a single color for each indicium or different colors for each indicium.

Figure 3:
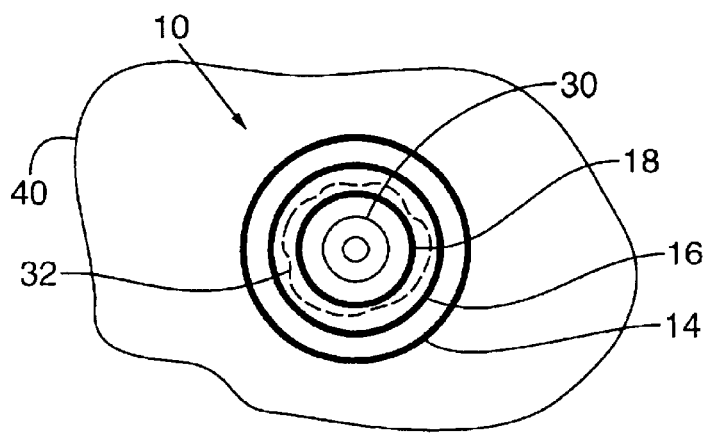
FIG. 3 illustrates use of the temporary tattoo of FIG. 1 as it is applied to skin to monitor a local reaction associated with a vaccination injection.

FIG. 3 illustrates a temporary tattoo 10 in place on the surface of a subject's skin 40 and centered on an injection site. The actual injection site is covered by a band-aid 30. In this illustration the band-aid 30 is disc shaped as shown in FIG. 3. Other band-aid shapes can be used, although they may tend to cover at least some of the local reaction. The three indicia 14, 16, and 18 are generally placed so that the actual injection site is centered within them. A hypothetical local reaction 32 is shown in phantom lines in FIG. 3. Assuming the inner indicium 18 represents a typical or normal local reaction, the middle indicium 16 represents a potentially abnormal inflammatory response that elicits cautious monitoring (e.g., watch carefully), and the outermost indicium 14 indicates an abnormal or excessive inflammatory response for which medical advice and/or attention is advised. The extent of the local reaction 32 in FIG. 3 suggests, that although medical advice and/or attention is not necessary at the present time, careful observation for any further worsening of the local reaction is warranted. Should the local reaction 32 tend to increase in area so as to cover or expand beyond indicium 18, the monitor (such as the parent, guardian, or subject) is recommended to contact appropriate medical personnel to relay relevant medical information (including, for example, extent of local reaction relative to the indicia, other symptoms the subject may be experiencing, and the like) to determine if clinical attention (such as a doctor's visit) is warranted. In most cases, the extent of the local reaction will be within normal parameters (i.e., within indicium 18) and no further follow-up will be required. Moreover, the monitor's concern or apprehension should be greatly decreased since the method provides a clear indication of the local reaction normally expected. This may be especially beneficial to first-time parents as they begin a child's immunization program.

In most cases, the temporary tattoo is designed to remain in place for about 3 to about 7 days. The design and/or coloring of the indicia may be selected to be visible with various skin tones and/or colors. The areas between the indicia 14, 16, and 18, or the indicia made up of line segments 54A–C, 56A–C, and 58A–C are ideally devoid of designs and colors so as not to obscure or hide any local reaction that may occur. Temporary tattoos in a variety of colors can be used so that a health care provider can selected an appropriate color combination that will be visible with the subject's particular skin color and/or tones.

In operation, the temporary tattoo is placed on the skin before or after the actual injection, for example, by placing the patch on the subject's skin and applying pressure to the patch. If the tattoo is placed on the skin before the injection, the injection is made, for example, in the center of the tattoo. If the tattoo is positioned after the injection, the tattoo is placed adjacent to the injection site, and may be, for example, centered on the injection site. The tattoo may be positioned before or after the band-aid is applied. Although FIG. 3 illustrates the use of the temporary tattoo with a band-aid covering the actual injection site, the band-aid is not necessary, and monitoring can be performed with or without the band-aid. If a band-aid is placed over the injection site at the time of the injection, it can be removed at a later time if desired. Furthermore, if desired, a new band-aid can be used, taking care not cover a significant portion of the markings. The temporary tattoo is placed around the site of the injection in a manner that avoids contamination and/or infection of the injection site. For example, the band-aid or other protective device may be placed over the injection site before application of the tattoo. If desired, a combination band-aid and temporary tattoo can also be used.

Conventional temporary tattoos can be used in the practice of this method. For example, suitable temporary tattoos and methods for making suitable tattoos are described in U.S. Pat. No. 5,817,385 (Oct. 6, 1998); U.S. Pat. No. 5,928,797 (Jul. 27, 1999); U.S. Pat. No. 5,958,560 (Sep. 28, 1999); U.S. Pat. No. 6,042,881 (Mar. 28, 2000); U.S. Pat. No. 6,074,721 (Jun. 13, 2000); and U.S. Pat. No. 6,106,852 (Aug. 22, 2000). Procedures for manufacturing and applying such tattoos are well known.

Specific procedures and/or instructions for applying the temporary tattoos from the manufacturer or supplier are often provided. General guidelines relating to application and use of one of the embodiments of the temporary tattoo for monitoring vaccination injections are as follows:

1. Clean skin area, for example by swabbing the skin with alcohol so that the tattoo is applied to skin that is clean and free from oils. Swabbing with alcohol also cleans both the injection site and the area to which the temporary tattoo will be applied, but the alcohol is allowed to dry before the tattoo is applied to the skin. In subjects having hairy skin, the area to which the tattoo is to be applied may also be shaved, or otherwise treated, to remove excessive hair.

2. Vaccinate using recommended procedures as supplied by the vaccine manufacturer or supplier.

3. Apply appropriate band-aid (preferably circular), taking care to center band-aid over the injection site.

4. Remove center circle of tattoo (i.e., hole 20 in FIGS. 1 and 2) if present. Peel the paper backing sheet off the patch. Place patch, face down, on the skin with the band-aid centered. Apply wet paper towel to the patch, taking care not to move the patch. Hold paper towel for about 30 seconds, saturating skin and patch liberally. Throw away paper towel and carefully peel off the tattoo's backing by separating the patch from the subject's skin. Allow the tattoo to air dry during post vaccination observation period.

5. Instruct subject and/or monitor on proper use and care of the tattoo. Discuss significance of various markings and actions to take based on observations of local reaction relative to markings. Once the tattoo has been applied, subjects may shower and bathe as usual, except the tattoo area should only be gently washed and should be blotted with a towel for drying. To enhance the tattoo's lifetime, it should not be scrubbed or rubbed vigorously. If desired, the band-aid may be removed at home, taking care not to damage the tattoo.

An example of a kit for use in performing the method is made up of a temporary tattoo on a patch and written instructions regarding use of the tattoo. The instructions provided in the kit might, for example be directed both to a person applying the temporary tattoo and to a subject and/or monitor. The instructions to a person applying the tattoo could explain the proper procedures to use in application of the tattoo. The instructions to a subject and/or monitor might, for example, explain how to care for the temporary tattoo, the significance of the indicia and how the indicia might be used to calibrate the inflammatory response, and what action to take if the local reaction extends beyond a particular indicium. The written instructions could be provided, for example, on the tattoo or the patch, separately from the tattoo or patch, or provided in a combination of instructions on the tattoo or patch and instructions provided separately.

In view of the many possible embodiments to which the principles of this method apply, it will be recognized that the specific illustrations disclosed herein should not be interpreted to limit the scope of the invention. Rather, the scope of the invention is in accord with the spirit of the following claims.

That which is claimed is:

1. A method for monitoring a local reaction due to an injection at an injection site on a subject's body, said method comprising:

placing a temporary tattoo on the subject's body adjacent to the injection site, wherein the temporary tattoo comprises at least one indicium spaced from, and centered on, the injection site; and observing the local reaction that may occur associated with the injection relative to at least one indicium;

wherein at least one indicium is a normal reaction indicium which represents the extent of a normal local reaction to the injection; wherein, if the local reaction remains within the normal reaction indicium, the local reaction is considered within normal parameters; and wherein, if the local reaction extends beyond the normal reaction indicium, the local reaction is considered outside of normal parameters.

2. The method of claim 1, wherein the indicium comprises a plurality of indicia surrounding the injection site.

3. The method of claim 2, wherein the plurality of indicia comprises three concentric indicia, including an inner indicium, a middle indicium, and an outermost indicium, with the inner indicium representing the extent of the normal local reaction.

4. The method of claim 2, wherein the plurality of indicia comprises three concentric indicia, including an inner indicium, a middle indicium, and an outermost indicium, with either the middle or outermost indicium representing the extent of the normal local reaction.

5. The method of claim 2, wherein the plurality of indicia are color coded.

6. The method of claim 2, wherein the plurality of indicia consists of three concentric circular indicia, including an inner indicium, a middle indicium, and an outermost indicium, with the inner indicium representing the extent of the normal local reaction.

7. The method of claim 1, wherein at least one indicium is circular.

8. The method of claim 1, wherein the injection is a vaccination or immunization shot.

9. The method of claim 1, wherein the injection is an allergy test.

10. The method of claim 1, wherein the injection is an insect sting or bite.

11. The method of claim 1, wherein at least one indicium is labeled.

12. A method for monitoring a local reaction due to an injection at an injection site on a subject's body, said method comprising:

placing a temporary tattoo on the subject's body adjacent to the injection site, wherein the temporary tattoo has at least one indicium spaced from, and centered on, the injection site; and observing the local reaction that may occur associated with the injection relative to the indicium;

wherein the indicium is placed in a relationship to the injection site that assesses a statistically normal reaction to the injection.

13. A temporary tattoo for assessing an inflammatory response to an injection, comprising:

a temporary tattoo transfer substrate; and a temporary tattoo on the temporary tattoo transfer substrate, wherein the temporary tattoo has at least one indicium for assessing an inflammatory response to an injection, and wherein the temporary tattoo has an integral label denoting a normal response to the injection.

* * * * *